United States Patent [19]

Pedersen et al.

[11] 4,408,071

[45] Oct. 4, 1983

[54] PROCESS FOR THE PRODUCTION OF CARBOXYLIC ACIDS

[75] Inventors: S. Erik Pedersen, Mentor; Harley F. Hardman, Lyndhurst; Louis F. Wagner, Solon, all of Ohio

[73] Assignee: Standard Oil Company, Cleveland, Ohio

[21] Appl. No.: 262,077

[22] Filed: May 11, 1981

[51] Int. Cl.$^3$ ................. C07C 51/235; C07C 51/255; C07C 53/08; C07C 63/06
[52] U.S. Cl. ............... 562/536; 423/415 A; 423/437; 562/421; 502/212
[58] Field of Search ............ 562/421, 536, 531; 252/435, 437

[56] References Cited

U.S. PATENT DOCUMENTS

| | | | |
|---|---|---|---|
| 1,985,750 | 12/1934 | Thomas et al. | 562/607 |
| 2,578,306 | 12/1951 | Hull | 562/531 |
| 3,103,535 | 9/1963 | Whitfield et al. | 562/531 |
| 3,655,747 | 4/1972 | Sennewald et al. | 562/531 |
| 4,094,901 | 6/1978 | Schaum et al. | 562/531 |

*Primary Examiner*—Vivian Garner
*Attorney, Agent, or Firm*—David P. Yusko; Herbert D. Knudsen; Larry W. Evans

[57] ABSTRACT

Aldehydes, such as acetaldehyde, are oxidized to carboxylic acids, such as acetic acid, by contacting the aldehyde with oxygen at oxidative conditions in the presence of a catalyst of the empirical formula $$Mo_{12}P_{0.1-3}Cu_{0.01-2}V_{0.1-3}M_{0.1-3}M'_{0.01-3}O_x \qquad (I)$$

where
M is at least one of K, Rb, Cs and Tl;
M' is at least one of Be, Mg, Ca, Sr, Ba, Nb, Ti, Zr, Ta, Mn, Fe, Co, Ni, Zn, Ag, Al, Ge, Sn, Pb, As, Bi, Te, Ce, Th, U and Sb; and
x is a number that satisfies the valence requirements of the other elements present.

12 Claims, No Drawings

PROCESS FOR THE PRODUCTION OF CARBOXYLIC ACIDS

BACKGROUND OF THE INVENTION

1. Field of the Invention

This invention relates to catalysis. In one aspect, the invention relates to the catalytic oxidation of an aldehyde to the corresponding carboxylic acid while in another aspect, the invention relates to the use in this oxidation of a promoted, phosphomolybdic oxide catalyst.

2. Description of the Prior Art

Various methods are known for converting aldehydes to carboxylic acids, particularly acetaldehyde to acetic acid. For example, Thomas et al., U.S. Pat. No. 1,985,750, teach the oxidation of acetaldehyde to acetic acid in the presence of manganic salts, particularly manganic acetate. Whitfield and Kemp, U.S. Pat. No. 3,103,535, teach the production of aliphatic carboxylic acids by contacting an aldehyde with a gas containing free oxygen in the presence of one or more metals of variable valency and phosphate ions. Sennewald et al., U.S. Pat. No. 3,655,747, also teach the production of carboxylic acids by the oxidation of aliphatic aldehydes with oxygen but in the presence of a carrier catalyst containing metallic palladium and/or palladium oxide and/or a palladium salt and at least one other metal, such as platinum, rhodium, ruthenium, etc. Other processes are known and some of these involve sensitive intermediates, such as a method currently in industrial use for preparing acetic acid which utilizes a peroxy acetic acid intermediate a compound with considerable explosive potential. Still other methods are known, including those taught by Hull, U.S. Pat. No. 2,578,306 and Schaum et al., U.S. Pat. No. 4,094,901.

SUMMARY OF THE INVENTION

According to this invention, acetic acid and benzoic acid are prepared from acetaldehyde and benzaldehyde, respectively, by a process comprising contacting at oxidative conditions the aldehyde with oxygen in the presence of a catalyst of the formula

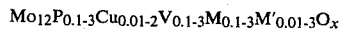

$$Mo_{12}P_{0.1-3}Cu_{0.01-2}V_{0.1-3}M_{0.1-3}M'_{0.01-3}O_x \quad (I)$$

where
M is at least one of K, Rb, Cs and Tl;
M' is at least one of Be, Mg, Ca, Sr, Ba, Nb, Ti, Zr, Ta, Mn, Fe, Co, Ni, Zn, Ag, Al, Ge, Sn, Pb, As, Bi, Te, Ce, Th, U and Sb; and
x is a number that satisfies the valence requirements of the other elements present.
This process is characterized by excellent aldehyde conversion, carboxylic acid selectivity, and the absence of a peroxy acid intermediate. Since the principle byproducts of this process are the carbon oxides, product recovery and purification are simple and inexpensive.

DETAILED DESCRIPTION OF THE INVENTION

Aldehydes

Acetaldehyde and benzaldehyde are the aldehydes used in this invention. Accordingly, as here used the term "aldehydes" means acetaldehyde and benzaldehyde and the term "carboxylic acids" means acetic acid and benzoic acid. These aldehydes are well known in the art and are available in commercial quantities. Both purified and technical grade aldehydes can be used in the practice of this invention and if desired, they can be diluted with other materials, such as nitrogen, other aldehydes, steam, etc.

Catalyst

The catalytic composition used in this invention is at least a 7 element material, i.e. a material containing molybdenum, phosphorus, copper, vanadium, alkali metal or thallium (M), at least one metal M', and oxygen all in designated, proportional amounts. Preferably, the subscript value of phosphorus in formula I is about 0.8 to 1.5, of copper about 0.2 to 0.8, of vanadium about 0.2 to 0.8, of M about 1 to 3 and M' about 0.1 to 2.5.

Preferred catalysts here used are those where M is at least one of potassium, rubidium and cesium and M' is at least one of antimony, barium, beryllium, magnesium, calcium, strontium and niobium. These preferred catalysts demonstrate unusually good aldehyde conversions and carboxylic acid selectivities, particularly those where M' is antimony, barium, bismuth or beryllium.

As is taught by formula I, certain of the components can be combinations of two or more elements, e.g. M' can be a combination of barium and niobium. In such instances, the subscript value represents the sum of the elements (e.g. for M', the sum of barium and niobium is a number within the range from about 0.01 to 2). Generally M and M' each represent but a single element.

Particularly preferred catalytic compositions here used are oxide compositions where M' is antimony, barium and/or bismuth, and the subscript value of M is at least one.

The exact structure or element arrangement of the catalysts here used are not known but the metal and phosphorus components are present in the form of their oxides, acids or oxide or oxyacid complexes. However the compositions of formula I are known not to be a mere physical mixture of their components but rather catalytic compositions where the individual components are chemically and/or physically bonded to one another.

The catalytic compositions used in this invention can be used in either the 100% active form or in a diluted form, i.e. supported or unsupported. Suitable support materials include silica, titania, alumina, zirconia, silicon carbide, boron, various phosphates, etc., with low surface area (about 1 m²/g) alumina a preferred support material. If a support is used, the catalytic composition is generally present in an amount of at least about 10 wt %, based on the combined weight of the support and the catalytic composition, and preferably in an amount of at least 30 wt %.

The catalytic compositions here used can be prepared in any one of a number of different methods, the particular method employed being a matter of convenience. Typically, the catalysts are prepared by mixing the appropriate catalyst ingredients in the proper proportions in an aqueous mixture, adjusting the pH of the mixture to about 4-7, drying the resulting aqueous slurry, and calcining the product. The ingredients can be added in any order during the preparation procedure but certain orders are preferred, particularly the mixing of the metallic ingredients prior to the addition of phosphorus (generally in the form of phosphoric acid). The ingredients employed can be the oxides, halides, nitrates, hydroxides, acetates or other salts of the particular metals or elements added, and particularly preferred is the use of water soluble salts of the metal components.

If a support is used, the material comprising the support may be incorporated into the catalyst along with the other ingredients or the catalyst composition may be coated and/or impregnated onto or into a support core. After the catalyst ingredients have been combined to form an aqueous slurry, the slurry is taken to dryness and the dried solid obtained is heated in the presence of air, nitrogen, nitric oxide or a mixture of any two or more of these gases at a temperature sufficient to effect calcination. This calcination can take place outside the catalytic reactor or an in situ activation can be utilized. Other methods of preparation are known and broadly taught in the art.

Aldehyde Oxidation

The compositions of formula I are highly effective catalysts for the oxidation of acetaldehyde and benzaldehyde to acetic and benzoic acid, respectively. These catalytic compositions are used in the same manner as known catalysts for these reactions. These reactions generally involve the contact of a gaseous aldehyde with molecular oxygen at an elevated temperature in the presence of a catalytic amount of catalyst. Exemplary of these known processes is the contacting of gaseous acetaldehyde with molecular oxygen in the presence of steam at a temperature between about 200° C. and about 400° C., preferably between about 250° C. and about 380° C., and most preferably between about 280° C. and about 350° C. The ratio of the reactants can vary widely with molar ratio of molecular oxygen to aldehyde of about 1 to 5 being typical. The amount of steam can also vary widely from none to a small amount generated in the reaction to 20 or more moles of steam per mole of aldehyde. Preferably, about 1 to 10 moles of steam per mole of aldehyde is employed in the reactant feed. In certain embodiments of this invention, other gases (principally nitrogen, oxygen, carbon dioxide and carbon monoxide) can be used with or instead of steam. Oxygen is most conveniently added as air.

The oxidation reaction can be conducted in almost any kind of reactor, e.g. fixed-bed, fluid-bed or transfer-line, using atmospheric, superatmospheric or subatmospheric pressure. The contact time of the reactants over the catalyst can vary from a fraction of a second to 20 or more seconds, the exact time dependent upon other reaction conditions, such as catalyst composition, feed composition, temperature, pressure, reactor design, etc.

The following examples are illustrative of certain specific embodiments of this invention. Unless otherwise indicated, all parts and percentages are by weight and the following conventions are used throughout:

AA = acetaldehyde
AcA = acetic acid
$VVH^{-1}$ = volume of AA per volume of catalyst per hour.

The oxygen subscript "x" in the catalysts of the examples is defined from the atomic ratios and valences of the other elements of the catalysts.

SPECIFIC EMBODIMENTS

Catalyst Preparation

The catalysts used in the following examples were prepared by dissolving, with stirring, ammonium heptamolybdate in distilled water and heating the resulting solution to 30°–35° C. While continuously stirring the solution and maintaining its temperature, an alkali metal hydroxide and the hydroxide or salt of M' was added. After 15 minutes aqueous solutions of copper acetate and ammonium metavanadate were sequentially added followed by concentrated hydrochloric acid. This mixture was then heated to 70° C. and stirred at that temperature for about 2 hours. After cooling to room temperature, phosphoric acid was added and the pH of the mixture was adjusted to about 5.6 with ammonium hydroxide. The mixture was then evaporated to dryness with stirring on a hot plate and the resulting solid was dried overnight at 110° C. The solid material was screened and the fines that went through a 50 mesh screen (U.S. Standard) were then used to coat a support. The powder was coated onto ⅛ in. Alundum ®spheres (alumina supports) so that the powder coatings (i.e. the catalysts) constituted about 35 wt % of the coated spheres. Water was used as the wetting agent in the amount of about 4% by weight of the Alundum ®.

Process Procedure and Conditions

The reactions were conducted in a 20 cc downward-flow, fixed-bed reactor equipped with a suitcase jacket heater. All examples were performed in the same manner: After drying in a 110° C. oven overnight, first the catalysts were exposed for one hour at 340° C. and then for an additional hour at 370° C. to an airflow (no feed) and second, the temperature of the reactor was then decreased to about 320° C. and the catalyst exposed to the feed (charging gas). After a short stabilization period, monitoring of the reaction progress was commenced over an extended time. The off-gas effluent was measured with a soap-film meter and the off-gas composition was determined with the aid of a Carle 111 gas chromatograph. The entire scrubber liquid of each sample was diluted with distilled water to about 200 g. A weighed amount of valeric acid was used as an internal standard in a 10% aliquot of the dilute solution. A one microliter sample was then analyzed in a Hewlett-Packard Model 5710A gas chromatograph fitted with a flame ionization detector and a FF Polyester column, 60/80 mesh. The split between the various acids was determined from the gas chromatographic analysis. The process conditions and results of these experiments are reported in Table I.

TABLE I

| | | ACETALDEHYDE OXIDATION[1] | | | | | |
|---|---|---|---|---|---|---|---|
| | | Time on Stream[2] (hrs.) | Jacket Temp.[3] (°C.) | AA Conv. | PPC[4] to | | Carbon Balance |
| Example | Catalyst | | | | AcA | CO + $CO_2$ | |
| 1 | $Mo_{12}P_{1.33}K_{1.5}Cu_{0.25}V_{0.25}Ba_{0.1}O_x$ | 8.5 | 320 | 94.6 | 77.3 | 16.1 | 95.6 |
| 2 | $Mo_{12}P_{1.33}Rb_{1.5}Cu_{0.25}V_{0.25}Ba_{0.1}O_x$ | 1.4 | 330 | 95.4 | 78.5 | 15.6 | 105.8 |
| 3 | $Mo_{12}P_{1.33}Cs_{1.5}Cu_{0.25}V_{0.25}Ba_{0.1}O_x$ | 2.5 | 330 | 99.0 | 82.8 | 15.4 | 102.1 |
| 4 | $Mo_{12}P_{1.33}K_{1.5}Cu_{0.25}V_{0.25}Bi_{0.25}O_x$ | 6.4 | 310 | 98.7 | 85.4 | 12.4 | 105.6 |
| 5 | $Mo_{12}P_{1.33}K_{1.5}Cu_{0.25}V_{0.25}Be_{0.2}O_x$ | 3 | 330 | 97.5 | 79.5 | 17.3 | 102.5 |

TABLE I-continued

| | | ACETALDEHYDE OXIDATION[1] | | | | | |
|---|---|---|---|---|---|---|---|
| | | Time on Stream[2] (hrs.) | Jacket Temp.[3] (°C.) | AA Conv. | PPC[4] to | | Carbon Balance |
| Example | Catalyst | | | | AcA | CO + $CO_2$ | |
| 6 | $Mo_{12}P_{1.33}K_{1.5}Cu_{0.25}V_{0.25}Sb_{0.25}O_x$ | 1.5 | 330 | 96.2 | 80.6 | 14.7 | 101.9 |
| | | 3.7 | 350 | 100 | 81.1 | 18.3 | 104.1 |
| | | 4.8 | 300 | 87.4 | 78.0 | 8.3 | 102.3 |
| | | 6.0 | 280 | 72.2 | 65.6 | 5.5 | 104.9 |

[1] For all examples, atmospheric pressure was used, the AA/Air/$H_xO$/$N_2$ mole ratio was 1/5/3.89/1.3, and the contact time was between 3 and 4 seconds.
[2] Measured from first introduction of charge gas (AA/Air/$H_2O$/$N_2$) to extraction of sample.
[3] Actual temperature within the reactor is slightly (15–20° C.) higher due to a small reaction exotherm.
[4] Per Pass Conversion to:
$$AcA = \frac{\text{Grams of carbon as AcA}}{\text{Grams of carbon as AA}} \times 100$$
$$Co + Co_2 = \frac{\text{Grams of carbon as Co and } Co_2}{\text{Grams of carbon as AA}} \times 100$$

Examples 1–3 demonstrate the use of catalysts differing only in the definition of their M component. All show good per pass conversion to AcA.

Examples 4–6 demonstrate the use of catalysts differing only in the definition of their M' component. All show good per pass conversion to AcA with Example 6 demonstrating the effect of temperature on per pass conversion. As can be seen, a lower temperature generally results in a lower conversion of AA with a resulting lower per pass conversion.

Although the invention has been described in considerable detail through the preceding examples, these examples are for the purpose of illustration only and it is understood that variations and modifications can be made by one skilled in the art without departing from the spirit and scope of the invention.

What is claimed is:

1. A process for preparing a carboxylic acid from an aldehyde, the process comprising contacting a gaseous aldehyde selected from the group consisting of acetaldehyde and benzaldehyde with oxygen in the presence of a catalyst of the formula $$Mo_{12}P_{0.1-3}Cu_{0.01-2}V_{0.1-3}M_{0.1-3}M'_{0.01-3}O_x \quad (I)$$

where

M is at least one of K, Rb, Cs and Tl;

M' is at least one of Be, Mg, Ca, Sr, Ba, Nb, Ti, Zr, Mn, Fe, Co, Ni, Zn, Ag, Al, Ge, Sn, Pb, As, Bi, Te, Ce, Th, U and Sb; and x is a number that satisfies the valence requirements of the other elements present.

2. The process of claim 1 where M is K, Rb or Cs.

3. The process of claim 2 where M' is at least one of Be, Mg, Ca, Sr, Ba, Nb, Bi and Sb.

4. The process of claim 2 where M' is at least one of Be, Sb, Ba and Bi.

5. The process of claim 4 where the subscript value of phosphorus in formula I is about 0.8 to 1.5, of copper about 0.2 to 0.8, of vanadium about 0.2 to 0.8, of M about 1 to 3 and of M' about 0.1 to 2.5.

6. The process of claim 5 where the catalyst is used with a support.

7. The process of claim 6 where the contacting is conducted at a temperature of about 200° C. to about 400° C.

8. The process of claim 6 where the contacting is conducted at a temperature of about 280° C. to about 350° C.

9. The process of claim 8 conducted in the presence of steam.

10. The process of claim 9 where the aldehyde is acetaldehyde.

11. The process of claim 10 where the molar ratio of oxygen to acetaldehyde is about 1 to 5.

12. The process of claim 11 where the support is a low surface area alumina.

* * * * *